United States Patent [19]

Mehlhardt et al.

[11] Patent Number: 4,458,531

[45] Date of Patent: Jul. 10, 1984

[54] METHOD OF AND APPARATUS FOR EXAMINING BIOLOGICAL EFFECTS IN CELL-LOTS

[76] Inventors: Wolfgang Mehlhardt, Im Grün 24, 7500 Karlsruhe 51; Fritz-Albert Popp, Hammanstrasse 15, 6520 Worms; Martin Rattemeyer, Grosselheimer Strasse 4; Hans-Günther Schmidt, Gladenbacher Weg 18, both of 3550 Marburg, all of Fed. Rep. of Germany

[21] Appl. No.: 311,009

[22] Filed: Oct. 13, 1981

[30] Foreign Application Priority Data

Oct. 10, 1980 [DE] Fed. Rep. of Germany ....... 3038255
Oct. 30, 1980 [DE] Fed. Rep. of Germany ....... 3040855

[51] Int. Cl.³ ............................................... G01T 1/00
[52] U.S. Cl. ............................... 73/432 R; 250/361 C; 436/63
[58] Field of Search ......................... 73/432 Z; 436/63; 250/361 C

[56] References Cited

U.S. PATENT DOCUMENTS

| | | | |
|---|---|---|---|
| 3,359,973 | 12/1967 | Hoffman | 250/361 C |
| 3,679,312 | 7/1972 | Mansberg | 250/361 C |
| 3,849,653 | 11/1974 | Sakaide | 250/361 C |
| 4,350,890 | 9/1982 | Geelhood et al. | 250/361 C |

Primary Examiner—S. Clement Swisher
Attorney, Agent, or Firm—Wenderoth, Lind & Ponack

[57] ABSTRACT

In a method of testing the biological effects of cell-lots, which release a characteristic or stimulatable ultra-weak photon radiation, the intensity and/or the photon statistic of the ultra-weak photon radiation is measured, as the test factor, for the purpose of the in vitro examination of substances for possible cell-damaging or regenerating effects, or for the purpose of carrying out quality control on biological substances, such as foodstuffs, edible plants or seed materials.

14 Claims, 3 Drawing Figures

METHOD OF AND APPARATUS FOR EXAMINING BIOLOGICAL EFFECTS IN CELL-LOTS

The invention relates to a method of examining biological effects in the case of cell-lots that release their own or stimulatable ultra-weak photon radiation.

The known methods of examining the biological effects of physical or chemical agents are based on subjecting the cell-lots to the examining agent either in an in vitro test i.e. as a cell culture, or in naturally occuring organisms, e.g. in plants or test animals in the in vivo test and under specific conditions. While taking into account the statistical distribution, dose-effect curves are established, which indicate the relationship between the dose of the dispensed agent and the parameter of the object that is to be investigated, such as for example the mutation rate. On the basis of the statistically evaluated results of measurements, conclusions can be drawn as regards the cell-damaging or cell-regenerating effects of certain agents, such as radiation, chemical substances and the like.

Because of the wide biological scatter, considerable expense is involved in carrying out tests of this kind. The admissibility of the use of these investigations is thus based on theory which differs from case to case.

A method of examining the biological effects in the case of cell-lots is also available in the examination of corresponding foodstuffs having a cellular structure. A known process for examining foodstuffs is based on irradiating the foodstuffs with blue or ultraviolet light and judging the colour characteristics of the reflected stray light. DE-OS No. 27 28 717 discloses the idea of determining the quality features of a test object consisting of meat by examining the beam emitted or reflected by the object, preferably in the visible or invisible light range, the wave-length and/or the intensity and/or the polarization being evaluated. However, this does not enable quality features, e.g. freshness, to be determined with sufficient accuracy.

DD-PS No. 117 743 describes a method of measuring damage sustained by agricultural products, for example potatoes, with the aid of fluorescence; wherein the object to be measured is treated with a chemical substance which, at the areas of damage, forms a compound which has a fluorescing effect and which when irradiated with ultra-violet light emits visible fluorescent light.

The object of the invention is to provide a method of examining biological effects in the case of cell-lots, which method permits specific highly sensitive examination of the biological condition of the cell-lots.

This object is achieved in that for the in vitro examination of substances for possible cell-damaging or regenerating effects or for the quality control of biological substances, such as biological foodstuffs (meat, food etc), edible plants (including medicinal plants) or seed or grain material, the intensity and/or the photon statistic of the ultra-weak photon emission is measured as the test factor.

The expression "ultra-weak photon emission", as used in the specification and the claims, means a wave radiation, the energy of which is less than the thermal radiation in the infra-red range by at least the factor $10^{-10}$. The ultra-weak photon emission, as the coherent characteristic radiation of objects, is differentiated from the incoherent thermal radiation etc., in that the intensity and wave-length relationships do not follow the Planck radiation law. Temperature differences cannot be used for measuring the ultra-weak photon emission. For this purpose, coherence measurements must be carried out on the photon statistic and/or the intensity of the radiation must be determined.

It is known from the publication "Electromagnetic Bio-Information" by F. A. Popp, G. Becker, H. L. König and W. Peschka, Edts. Urban & Schwarzenberg, Munich-Baltimore 1979 that biological systems, in particular living cells, emit an ultra-weak photon radiation, which depend upon various surrounding influences. The presence of such an ultra-weak photon emission is assumed in the present method, which derives the effect of agencies from their influence on the photon emission of biological systems and permits a comparison with the behaviour of undisturbed or decaying systems, the method also permitting the quality control of foodstuffs.

In principle, these investigations can be carried out on any form of cell-lots, particularly on a cell culture, but also on a test plant or an experimental animal. Since the intensity of the ultra-weak photon radiation and/or the photon statistic is characteristically altered by the effect of test substances, useful conclusions can be drawn regarding the effect mechanism and the general effectiveness of the agent, on the basis of measurements carried out prior to and during the action of the test substance. Instead of the hitherto usual dose-effect curve, plots are obtained in which the spectrally divided change, with time, in the intensity of the emitted radiation as well as characteristic parameters of the photon statistic, such as factorial moments, cumulants etc., may be advantageously represented in dependence upon the dose of the dispensed substance or the strength of the physical agent applied, e.g., of a thermal radiation. The plots so obtained are evaluated as regards intensity and the various possible coherence measurement of the photon statistic (see R. J. Glauber, Quantum Optics, Academic Press NY London, 1969).

The method may be advantageously modified by the specific use of further external effects, preferably magnetic and/or electrical D.C. or A.C. fields (wave radiation), or a light beam of specific wave-length which acts on the cell-lot.

In the quality control of biological substances, it is possible, for example, to judge the quality of biological fluids or the germinating power of seed material on the basis of the ageing condition if suitable comparative values are determined from a sample of substantially similar composition, for example by taste tests and/or chemical analysis, or by seeding tests. In particular, the freshness of foodstuffs, which depends mainly on healthy cell-lots, can be checked by measurement and by estimating the characteristic radiation. Furthermore the content of biologically harmful foreign substances, for example poisons such as spraying agents in the case of meat and plants, can be detected as residual materials.

In the case of biological samples having no pronounced characteristic radiation, it may be expedient to stimulate the sample prior to and/or during measurement of the photon emission by means of a magnetic and/or electrical D.C. or A.C. field. Such advantageous stimulation may also be achieved by means of a light beam of specific wave-length, for example 5,000 nm, or by means of elevated or low temperatures.

A further advantageous way of stimulating a sample having inadequate characteristic radiation involves specific excitation with the aid of chemical additives, e.g.

with intracellular toxins. Ethanol, for example, appears to be an advantageous possible additive. The stimulated characteristic radiation, like the natural characteristic radiation, likewise exhibits an intensity and/or photon statistic that is dependent upon the biological premises.

Advantageous apparatus for performing the method may be so constructed that, in a specific arrangement relative to a sample, i.e. at a certain distance from the sample, which may be placed in a vessel through which the photon radiation can pass, there is provided a photon sensor for ultra-weak photon radiation, which has considerable detection sensitivity in the wave/length range of between 10,000 nm and 200 nm that is to be investigated. The output of the sensor is increased by a measuring amplifier which is connected to a recording and/or display measuring instrument. Sensors having photo-cathodes made of alkaline metals and of substances consisting of several elements such as Na, K, Cs, Sb, have proved suitable. The measuring amplifier expediently takes the form of a known arrangement consisting of a photo-multiplier having a magnification factor $V > 10^6$.

Embodiments of the invention are illustrated diagrammatically in the drawings, in which.

Figure 1:
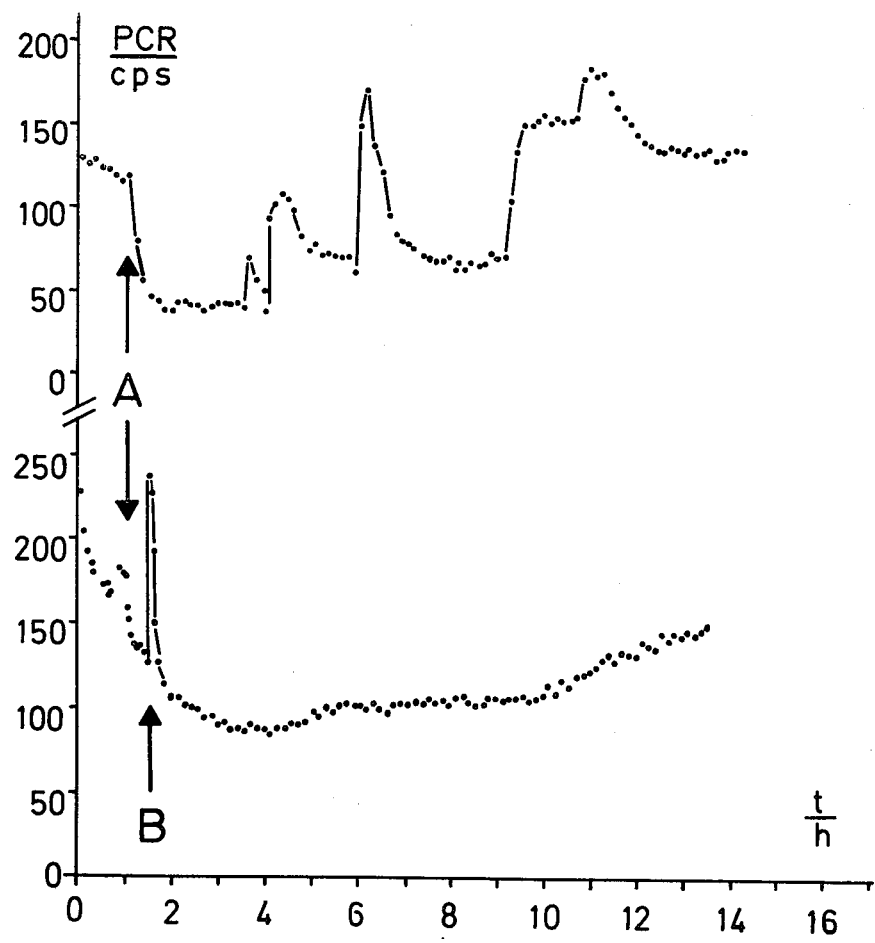
FIG. 1 illustrates the change in photon emission in the case of cucumber seeds.

The upper part of FIG. 1 shows the change in the photon emission of cucumber seeds as the Photon Count Rate, which seeds had been treated at the indicated moment A with the intra cellular toxin heparin. Immediately following addition of heparin, the radiation emission first dropped and after several hours then rose with fluctuations that become progressively more marked until, after approximately 11 hours a maximum rise is reached which, by a continuous drop to zero (not shown), indicates that the cell-lot is dead.

As can be seen in the lower part of FIG. 1, this change is inhibited by the counter-acting substance Protamin. Immediately after addition of the Protamin at the moment B which occurs roughly 30 minutes following the poison effect, there is first observed a spontaneous activity in the photon emission which, however, after a short time moves into a forward curve that is characteristic of healthy seeds.

Figure 2:
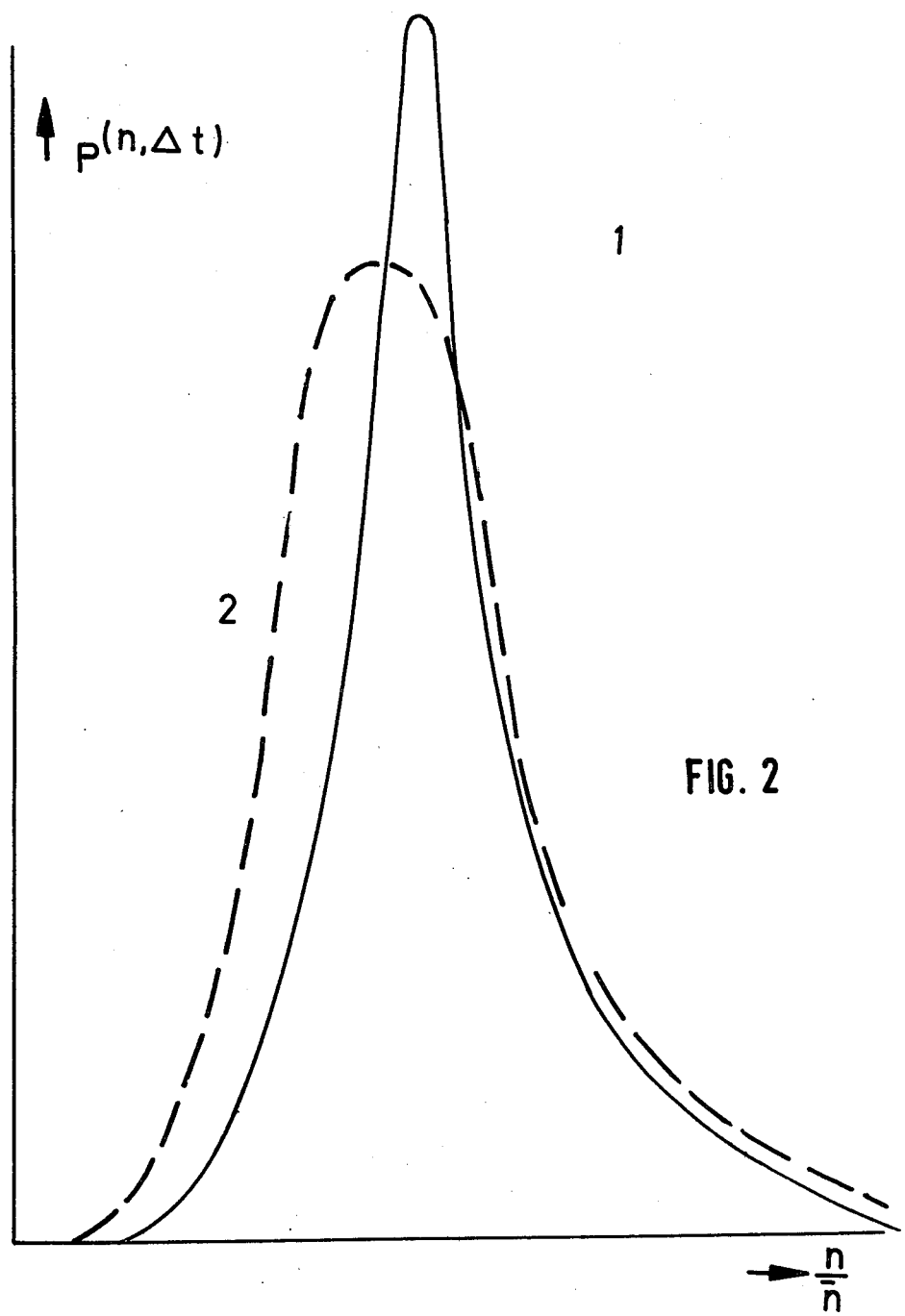
FIG. 2 illustrates the change in photon emission in the case of two samples of beetroot juices of different quality.

FIG. 2 relates to two samples of beetroot juice of different qualities. The samples were produced under comparable conditions by cold pressing and were stored for approximately two weeks before measurements were carried out.

Probability p (n, $\Delta t$), is plotted as the ordinate, n photon being recorded in the measuring time interval $\Delta t$. Each measurement is based on 300 values having a $\Delta t \approx 500$ ms. The relationship (n/$\bar{n}$) selected as the abscissae, with $\bar{n}$ as the average value for the number of photons in the measuring interval $\Delta t$. This ensures that different measurement curves can be directly compared with different average values. From the differing course of the curves and by means of preceeding chemical or sensor tests, it can be established that Sample 1, which has the smaller width of scatter in the dissolution curve, has a better biological quality than Sample 2, i.e. in this case a more natural taste.

The probability p (n, $\Delta t$) is referred to as the photon statistic and indicates the frequency with which n photon (n = 1, 2, 3 ... ) are emitted in a given measuring time interval $\Delta t$.

For the purpose of indicating further quality characteristics, additional values measured on the two samples may be used. These can be seen from the following table.

|  | Average value in | Scatter $\delta$ | Factorial moment 1st order | Deterioration parameter $\delta^2$ - m |
|---|---|---|---|---|
| Sample 1 | 40.86 counts | 10.56 counts | 0.04 counts | 1.73 |
| Sample 2 | 29.59 counts | 10.83 counts | 0.10 counts | 2.96 |
| Control | 21.92 counts | 9.53 counts | 0.14 counts | 3.14 |

Here a marked difference in the ultra-weak photon radiation is likewise indicated between two samples of foodstuff. Taking into account the control value, which corresponds to the empty vessel for accommodating the samples, the average value for the better Sample 1 is approximately twice as great as for the poorer Sample 2. It can also be seen that the factorial moments of the first order and the deterioration parameter differ significantly in the samples.

In the case of carcinogenous substances, and according to the known results of researches, it is assumed that functions are involved that are not absolutely dependent upon the nature of the investigated biological system. In general, the carcinogeneity of a substance is specific to the molecule and is therefore not dependent upon the nature of the biological system concerned. The same consideration also applies as regards mutageneity. Above all, there are no detectable fundamental differences between animal and plant tumours.

Thus, for the purpose of examining the carcinogeneity of a substance it generally suffices to go back to a cell-lot in the form of a test plant, which has a particularly pronounced and easily measurable photon emission. This applies for example as regards the cucumber seeds investigated in FIG. 1.

Under comparable conditions, the seeds are treated, on the one hand, with known non-carcinogenous substances of similar molecular configuration and, on the other hand, with the test substance (i.e. the agent), the carcinogeneity of which is to be tested. In both cases, the total intensity of the ultra-weak photon radiation is investigated in a specific spectral distribution.

If the photon statistic p (n $\Delta t$) varies less markedly in the direction of increased incoherence of radiation in the biological system than in the case of the non-carcinogenous comparison substance, then by comparing the change, with time, of the photon statistic, it can be concluded that the test substance does not have carcinogenous properties. Conversely, given incoherence criteria there can be precisely established that the carcinogenous effects of the test substance has to be taken into account.

Figure 3:
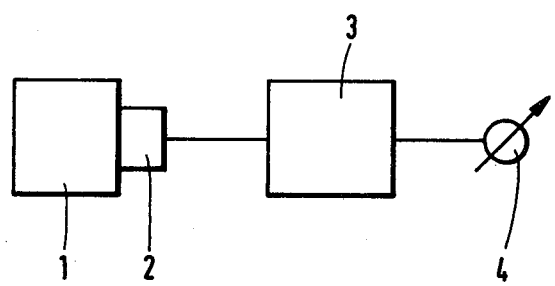
FIG. 3 illustrates a measuring arrangement.

FIG. 3 illustrates in a simple diagrammatic manner the measuring apparatus used in accordance with the invention. A quartz glass vessel 1 is provided for accommodating the cell culture that is to be investigated. In front of its outlet surface is a photon sensor 2 in the form of a photo-cathode. The output from the sensor is passed to a measuring instrument 4 by way of a measuring amplifier 3.

We claim:

1. A method of determining the occurrence of non-occurrence of a change in the biological state of cell-lots which emit their own or stimulatable ultra-weak photon radiation, which comprises measuring the intensity and/or the photon statistic of coherent ultra-weak photon radiation emitted by said cell-lots, and comparing said measurement with another said measurement taken with respect to said cell-lots.

2. A method according to claim 1, for examining the biological effects of physical and/or chemical agents on the cell-lots, wherein the ultra-weak photon radiation and the photon statistic of cell-lots are determined without applying the agent to the cell-lots, the photon radiation is determined following the effect of the agent as a photon statistic, and the agent is judged as to whether its effect is damaging or regenerating for the cell-lots on the basis of whether the photon radiation changes as compared to that for the cell-lots before application of the agent.

3. A method according to claim 2, wherein, before the photon statistic is recorded under the effect of the agent to be examined, a photon statistic is recorded under the effect of another agent of known effect, and the two photon statistics are compared for the purpose of judging the result of the examination.

4. A method according to claim 3, wherein, in the case of a chemical agent that is to be examined as regards its carcinogenous properties, a first photon statistic is determined on a non-carcinogenous substance of chemically similar structure, a second photon statistic is recorded on the agent to be examined, and the two photon statistics are compared with each other from the point of view of the incoherence of the radiation.

5. A method according to claim 1, for carrying out quality control on biological substances, wherein the intensity of the ultra-weak photon radiation and/or its photon statistic is measured as an indication of quality of the biological substance.

6. A method according to claim 5, wherein the biological substance is a foodstuff.

7. A method according to claim 5, wherein the intensity of the ultra-weak photon radiation and/or the photon statistic in correlation with known quality features is determined on the basis of visual, chemical, physical and/or sensor examination, the intensity of the ultra-weak photon radiation and/or its photon statistic is determined for the biological substance to be investigated, and the quality features are determined in accordance with known comparison values.

8. A method according to claim 5, wherein the biological substance is stimulated to photon radiation by additional chemical substances prior to and/or during the measurement.

9. A method according to claim 8, wherein ethanol is used for effecting stimulation.

10. A method according to claim 1, 2 or 5, wherein the intensity of the ultra-weak photon radiation and/or its photon statistic is measured separately in different zones of the spectrum of the radiation.

11. A method according to claim 1, 2 or 5, wherein a magnetic and/or electrical field also acts on the cell-lots prior to and/or during measurement of the ultra-weak photon radiation.

12. A method according to claim 1, 2 or 5, wherein a light beam of specific wave-length acts on the cell-lots.

13. An apparatus for performing the method of claim 1, 2 or 5, which comprises a test vessel provided with an outlet through which ultrasonic photon radiation can pass, a photon sensor positioned to receive the radiation from said outlet of said vessel, said sensor having detection-sensitivity in a radiation range to be investigated, an amplifier for increasing the output capacity of said sensor, and a measuring instrument connected to said amplifier.

14. An apparatus according to claim 13, wherein said sensor is a photo-cathode.

* * * * *